US010292670B2

(12) United States Patent
Hissoiny

(10) Patent No.: US 10,292,670 B2
(45) Date of Patent: May 21, 2019

(54) METHOD AND SYSTEM FOR DOSE CALCULATION BASED ON CONTINUOUS MATERIAL INDEXING

(71) Applicant: ELEKTA LTD., Montreal (CA)

(72) Inventor: Sami Hissoiny, Quebec (CA)

(73) Assignee: Elekta Ltd., Montreal (CA)

( * ) Notice: Subject to any disclaimer, the term of this patent is extended or adjusted under 35 U.S.C. 154(b) by 1207 days.

(21) Appl. No.: 14/271,862

(22) Filed: May 7, 2014

(65) Prior Publication Data

US 2015/0154374 A1  Jun. 4, 2015

Related U.S. Application Data

(60) Provisional application No. 61/911,999, filed on Dec. 4, 2013.

(51) Int. Cl.
*A61B 6/00* (2006.01)
*A61N 5/10* (2006.01)
(Continued)

(52) U.S. Cl.
CPC .......... *A61B 6/5217* (2013.01); *A61B 8/5223* (2013.01); *A61N 5/103* (2013.01);
(Continued)

(58) Field of Classification Search
CPC . G06F 19/3437; G06F 19/3481; A61N 5/103; A61N 5/1031; A61N 2005/1034; A61B 8/5223; A61B 6/5217; G16H 50/50
(Continued)

(56) References Cited

U.S. PATENT DOCUMENTS 5,341,292 A * 8/1994 Zamenhof ............ A61N 5/1031
                                                        600/410
5,381,518 A * 1/1995 Drebin .................... G06T 17/00
                                                        345/421
(Continued)

FOREIGN PATENT DOCUMENTS

CN           1778275 A      5/2006
CN         101028192 A      9/2007
(Continued)

OTHER PUBLICATIONS

Jabbari. "Review of Fast Monte Carlo Codes for Dose Calculation in RadiationTherapy Treatment Planning". J Med Signals Sens. Jan.-Apr. 2011; 1(1): 73-86.*

(Continued)

*Primary Examiner* — Eunhee Kim
(74) *Attorney, Agent, or Firm* — Schwegman Lundberg & Woessner, P.A.; Sanjay Agrawal

(57) ABSTRACT

A system and method for simulating energy transport between particles and an object in radiotherapy is provided. A three-dimensional representation, having a plurality of voxels, is generated for a portion of a patient to be treated. A material index for each of the plurality of voxels is determined. The material index has an identifier for a first boundary material corresponding to a voxel and a percentage of the voxel associated with a second boundary material. The method further comprises simulating energy transport between a particle and the object by calculating an amount of energy deposited by a particle within the patient based on the material indices of the voxels and a list of boundary materials.

25 Claims, 6 Drawing Sheets

(51) Int. Cl.
  *A61B 8/08* (2006.01)
  *G06F 19/00* (2018.01)
  *G16H 50/50* (2018.01)
(52) U.S. Cl.
  CPC .... *A61N 5/1031* (2013.01); *A61N 2005/1034* (2013.01); *G06F 19/3481* (2013.01); *G16H 50/50* (2018.01)
(58) Field of Classification Search
  USPC .......................... 703/6; 378/65, 901; 702/179
  See application file for complete search history.

(56) References Cited

U.S. PATENT DOCUMENTS

| | | | |
|---|---|---|---|
| 5,590,215 A | 12/1996 | Allen | |
| 5,640,496 A | 6/1997 | Hardy et al. | |
| 5,870,697 A * | 2/1999 | Chandler | A61N 5/1031 378/62 |
| 6,148,272 A | 11/2000 | Bergstrom et al. | |
| 6,175,761 B1 * | 1/2001 | Frandsen | A61N 5/1031 128/920 |
| 6,301,329 B1 | 10/2001 | Surridge | |
| 8,527,519 B2 | 9/2013 | Salemann | |
| 9,495,513 B2 * | 11/2016 | Yepes | A61N 5/1031 |
| 2002/0106054 A1 * | 8/2002 | Caflisch | A61N 5/103 378/65 |
| 2007/0282575 A1 * | 12/2007 | Gossage | G06F 17/5009 703/2 |
| 2012/0232375 A1 | 9/2012 | Zebaze et al. | |

FOREIGN PATENT DOCUMENTS

| | | |
|---|---|---|
| CN | 102648482 A | 8/2012 |
| WO | WO 01/45556 A1 | 6/2001 |
| WO | WO 2013/072874 A1 | 5/2013 |

OTHER PUBLICATIONS

B.R.B. Walters, et al. "DOSXYZnrc Users Manual Ionizing Radiation Standards National Research Council of Canada," *NRCC Report PIRS-794*, 2002.

Indrin J. Chetty, et al., "Report of the Aapm Task Group No. 105: Issues associated with clinical implementation of Monte Carlo-based photon and electron external beam treatment planning," *Medical Physics*, 34(12):4818-4853, 2007.

Iwan Kawrakow, et al., "3D electron dose calculation using a Voxel based Monte Carlo algorithm (VMC)," *Medical Physics*, 23(4):445-457, 1996.

J.V. Siebers, et al., "Converting absorbed dose to medium to absorbed dose to water for Monte Carlo based photon beam dose calculations," *Physics in Medicine and Biology*, 45(4):983, 2000.

Sami Hissoiny, et al., "GPUMCD: A new GPU-oriented Monte Carlo dose calculation platform," *Medical Physics*, 38(2):754-764, 2011.

M.J. Berger, et al., "XCOM: Photon Cross Section Database (version 1.5)," http://physics.nist.gov/xcom, 2010.

M.J. Berger, et al., "ESTAR, PSTAR, and ASTAR: Computer Programs for Calculating Stopping-Power and Range Tables for Electrons, Protons, and Helium Ions (version 1.2.3)," http://physics.nist.gov/Star, 2005.

"Tissue substitutes in radiation dosimetry and measurement," Technical Report No. 44, International Commission on Radiation Units and Measurements (ICRU), Bethesda, MD, 1989.

Matthias Fippel, "Fast Monte Carlo dose calculation for photon beams based on the VMC electron algorithm," *Medical Physics*, 26(8):1466-1475, 1999.

Iwan Kawrakow, "Improved modeling of multiple scattering in the Voxel Monte Carlo model," *Medical Physics*, 24(4):505-517, 1997.

International Search Report and Written Opinion of International Patent No. PCT/182014/066493, dated Mar. 10, 2015, 12 pages.

Extended European Search Report issued in corresponding International Application No. PCT/IB2014066493, dated May 15, 2017 (9 pages).

"Chinese Application Serial No. 201480064853.X, Office Action dated May 18, 2018", w/ English translation, 32 pgs.

* cited by examiner

Table 1

| Material | ρ g/cc | H | C | N | O | Na | Mg | O | S | Cl | K | Ca |
|---|---|---|---|---|---|---|---|---|---|---|---|---|
| | | | | | | % mass | | | | | | |
| Soft Tissue (ICRU44) | 1.06 | 0.102 | 0.143 | 0.034 | 0.708 | 0.002 | 0.000 | 0.003 | 0.003 | 0.002 | 0.003 | 0.000 |
| Cortical bone | 1.92 | 0.064 | 0.155 | 0.042 | 0.435 | 0.001 | 0.002 | 0.103 | 0.003 | 0.000 | 0.000 | 0.225 |
| 50% v/v Tissue - Bone | 1.49 | 0.058 | 0.151 | 0.039 | 0.532 | 0.001 | 0.001 | 0.067 | 0.003 | 0.001 | 0.001 | 0.145 |

FIG. 4

METHOD AND SYSTEM FOR DOSE CALCULATION BASED ON CONTINUOUS MATERIAL INDEXING

CROSS REFERENCE TO RELATED APPLICATIONS

This is a non-provisional application and claims the benefit of priority to U.S. Provisional Application No. 61/911,999, filed on Dec. 4, 2013, the entirety of which is incorporated by reference.

TECHNICAL FIELD

This patent application is related to simulating radiation transport for radiotherapy and, more particularly, simulating radiation transport based on continuous material indexing. However, it may be appreciated that the described techniques may find application in other medical applications.

BACKGROUND

Radiotherapy is commonly applied to treat cancerous tumors. During a radiotherapy session, a patient is subject to ionizing or non-ionizing radiation, which is designed to control or kill malignant cancerous cells. In addition to treating cancerous cells, however, radiotherapy may cause undesired side effects to the patient by damaging normal or healthy cells that are in proximity to the malignant cancerous cells in humans or animals. During radiotherapy, radioactive particles enter the patient's body and interact with the tissue and organs of the patient through radiation transport. Radiation transport refers to a process in which the radioactive particles transfer energy to the patient's body through the interaction with the tissue and organ, thereby subjecting the patient's body to radiation. Although mechanisms are employed to reduce radiation imparted to normal cells during radiotherapy, it is desired to simulate the radiation transport to estimate the amount of energy that the patient will receive before a treatment session, in order to facilitate treatment planning and management.

A Monte Carlo simulation is a commonly used method for simulating radiation transport in radiotherapy. According to the Monte Carlo simulation, the interactions between particles, such as photons or electrons, and patient's body are modeled as a stochastic process. The particle interactions are randomly sampled based on material properties of the tissues, in which the particles travel. These properties include, for example, mass stopping powers and mass scattering powers for charged particles, and mass attenuation coefficients for various types of discrete particle interaction.

In a conventional Monte Carlo simulation, the patient's body is modeled as a three-dimensional data set including a plurality of voxels. Each voxel may represent a value on a regular grid in three-dimensional space. Material information representing physical and material properties is defined for every voxel of the patient model. Based on the material information, the radiation transport may be determined by determining the distance traveled by a particular particle and the type of interaction between the particle and the voxels.

Two conventional approaches have been used to define the material information in a Monte Carlo simulation. One approach is the "no material" approach, where data representing physical properties is tabulated as a function of energy for water only. The data is then modified in each voxel on the basis of the mass density of the voxel with respect to the mass density of water. This approach, however, is typically very inflexible and does not allow the user to assign a specific medium to a particular voxel, in which the exact material composition is known. Furthermore, the "no material" approach may introduce significant systematic error in simulations, when metals or other high-atomic-number materials are present.

Another conventional approach is the "discrete material" approach, where every voxel is explicitly identified as containing a single defined material. A material may include a single element or several elements, whose proportions are specified either by mass for a mixture or by the number of atoms for a compound. However, a material medium is assigned to each patient voxel based solely on the information gathered during imaging.

As a result, the "discrete material" approach introduces discretization errors into the dose computation. For example, two voxels whose densities are respectively 1.100 g/cc and 1.102 g/cc are expected to have very similar material properties. However, the "discrete material" approach may characterize the former voxel to be soft tissue and the latter voxel to be bone. These two voxels include different materials with different mass densities and may interact differently with radioactive particles having the same energy.

In addition, the "discrete material" approach may cause discontinuous mappings between dose to medium (DTM) and dose to water (DTW). The choice between DTM and DTW affects which quantity is determined during the simulation, and thus, ultimately what is presented to the user. In the case of DTM, the actual deposited energy per unit mass received by the actual material is determined. In the case of DTW, the dose to a very small water volume embedded in the medium is determined. Conventional Monte Carlo algorithms may compute DTM, but historical dose algorithms frequently approximated tissue as water. The American Association of Physicists in Medicine has recommended that all radiotherapy planning systems report both DTM and DTW. Thus, a conversion between DTM and DTW is then often necessary. In the above example, the DTW/DTM ratio is about 1.01 for the purported "soft tissue" voxel and about 1.12 for the purported "bone" voxel. A difference of 11% in the DTM/DTW ratio may thus arise from a miniscule difference in mass density. To make the conversion between DTM and DTW smooth, new materials must be introduced that are gradated mixtures of soft tissue and bone. At least ten intermediate mixtures of soft tissue and bone must be defined in order to ensure that the discontinuity in the DTW/DTM ratio is never more than 1%.

As is evident from the foregoing, conventional techniques for simulating radiation transport for radiotherapy have several drawbacks. Accordingly, improvements in radiation transport for radiotherapy that overcome these drawbacks are needed.

SUMMARY OF THE DISCLOSURE

In accordance with an embodiment, a computer-implemented method for simulating energy transport between particles and an object in radiotherapy is disclosed. The method comprises identifying a plurality of boundary materials for the object and a plurality of identifications. Each of the plurality of identifications identifies one of the plurality of boundary materials. The method further comprises selecting from the plurality of boundary materials, a combination of a first boundary material and a second boundary material for a portion of the object based on a material property of the portion of the object. The method further comprises determining a material index for the portion of the object based on the combination of the first boundary material and the second boundary material and calculating an amount of energy deposited by a particle within the portion of the object based on the material index.

In accordance with another embodiment, a system for simulating energy transport between particles and a patient undergoing radiotherapy is disclosed. The system comprises a storage medium for storing computer-executable instructions and a processor for executing the computer-executable instructions. The instructions cause the processor to generate a three-dimensional representation of at least a portion of a patient. The three-dimensional representation includes a plurality of voxels. The instructions further cause the processor to determine a material index for each of the plurality of voxels based on boundary materials and identifiers assigned to the boundary materials. The material index for each voxel has a first part including an identifier of a first boundary material within the corresponding voxel and a second part including a percentage of the corresponding voxel associated with a second boundary material within the voxel. The instructions further cause the processor to calculate an amount of energy deposited by particles within the patient based on the material indices of the voxels and the list of boundary materials.

In accordance with another embodiment, a computer-readable medium including computer-executable instructions is disclosed. The instructions, when executed by a processor, cause the processor to perform a method for simulating energy transport between particles and an object in radiotherapy. The method comprises identifying a plurality of boundary materials for the object and a plurality of identifications. Each of the plurality of identifications identifies one of the plurality of boundary materials. The method further comprises selecting, from the plurality of boundary materials, a combination of a first boundary material and a second boundary material for a portion of the object based on a material property of the portion of the object, determining a material index for the portion of the object based on the combination of the first boundary material and the second boundary material, and calculating an amount of energy deposited by a particle within the portion of the object based on the material index.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate several embodiments of the disclosure and together with the description, serve to explain the principles of the disclosure. In the drawings:

FIG. 4 is a table with a list of exemplary boundary materials, according to an embodiment of the disclosure;

DESCRIPTION OF THE EMBODIMENTS

Figure 1:
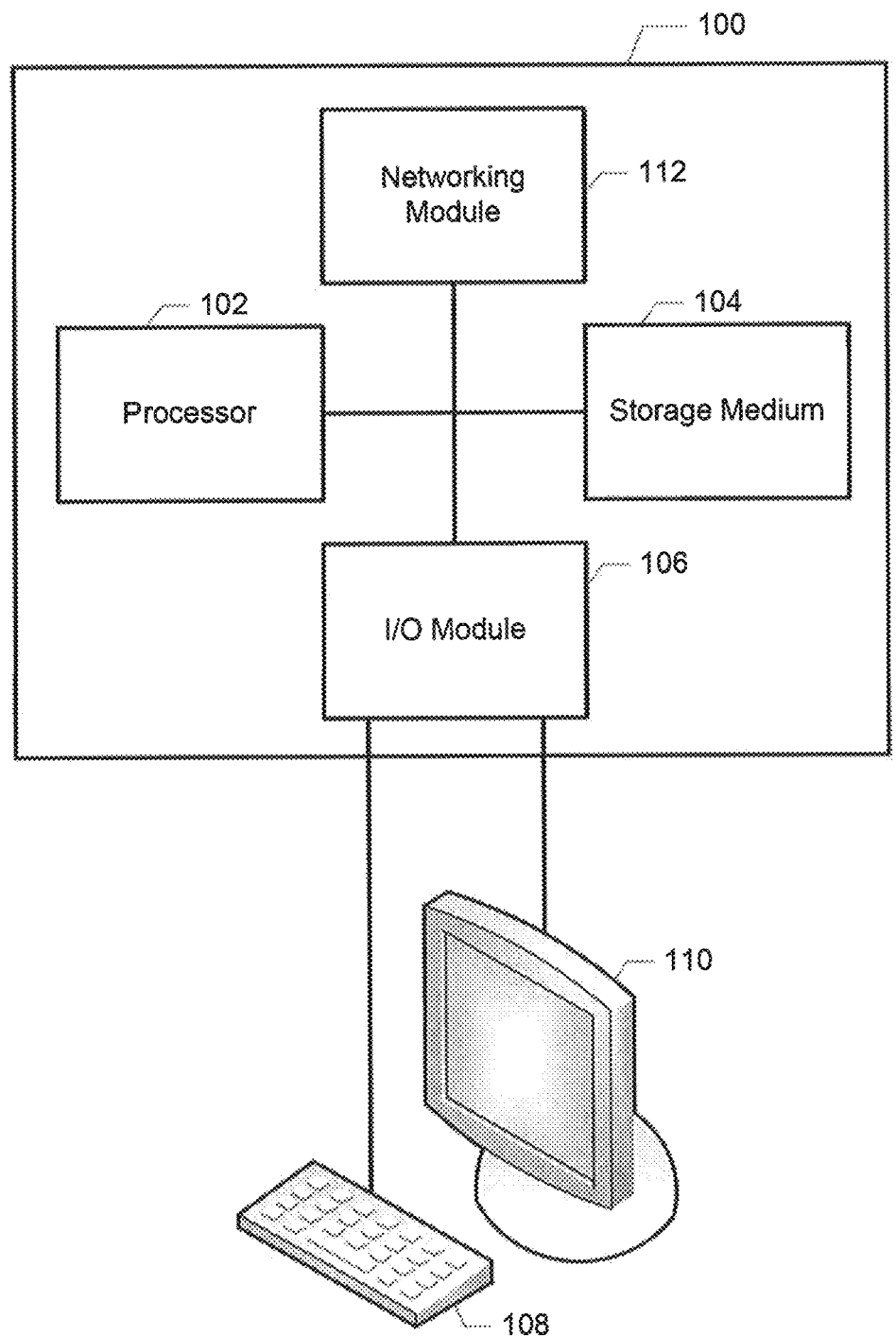
FIG. 1 is a diagram of a system for simulating radiation transport for radiotherapy, according to an embodiment of the disclosure.

Reference will now be made in detail to the disclosed embodiments, examples of which are illustrated in the accompanying drawings. Wherever possible, the same reference numbers will be used throughout the drawings to refer to the same or like parts.

According to the Monte Carlo technique, a patient's body that is subject to radiotherapy is modeled as a geometry or a three-dimensional data set including a plurality of materials. The three-dimensional data set includes a plurality of voxels, each including one or more materials. Physical data or properties for each material used in the simulation must be available a priori. The required data varies between Monte Carlo systems. Examples of material data sources include XCOM (Photon Cross Section Database), available at http://physics.nist.gov/xcom (accessed on Jan. 27, 2014) or ESTAR, PSTAR, and ASTAR (Computer Programs for Calculating Stopping-Power and Range Tables for Electrons, Protons, and Helium Ions), available at http://physics.nist.gov/Star (accessed on Jan. 27, 2014), all of which are incorporated by reference herein. The list of available materials is not specific to a given patient or treatment plan. An individual case may use only a subset of all defined materials.

Disclosed embodiments provide a continuous material indexing (CMI) technique, which defines, a priori, a plurality of boundary materials and their respective material information. During a Monte Carlo simulation, the material of a particular voxel is determined as a combination of at least two or more boundary materials. The percentages of the boundary materials within individual voxels may vary continuously from voxel to voxel.

According to an embodiment, a list of boundary materials may be defined to include, for example, air, tissue, and bone. Alternatively, various types of tissues may be defined, including, for example, epithelial tissue, connective tissue, muscle tissue (e.g., skeletal, smooth, or cardiac tissue), and nerve tissue. In the list, the boundary materials may be arranged in pairs and represented by, for example, (air, tissue) and (tissue, bone). Within each voxels, a combination or a mixture of the two materials may be defined according to various embodiments of this disclosure.

In another embodiment, individual materials in the list may occur multiple times, representing all possible pairs of boundary materials. For example, a list of boundary materials may include air, tissue, bone, and air, which allow all possible pairs of the three individual materials to be modeled. The boundary materials defined by the technique may be case-specific and are not limited to the exemplary embodiments described herein.

Disclosed systems and methods eliminate the need for multiple pre-defined material mixtures that are required by conventional methods. This may be accomplished by using a decimal number instead of an integer number to identify the material content of a voxel. The decimal number may be used to model the fact that a voxel is filled with a combination of two or more materials or substances, rather than only one material. Thus, even with a small number of pre-defined materials in the selected boundary materials, the disclosed method and system may provide a substantially greater number of combinations as well as smooth DTM/DTW conversions. This data representation may also better conform to the physical reality in which materials, such as a combination of air and soft tissue or a combination of bone and soft tissue, are not mixed homogeneously within a voxel, but rather occupy geometrically discrete portions of the voxel.

Disclosed systems and methods may be implemented in any Monte Carlo radiation transport simulations, such as the Graphics Processing Unit (GPU) Monte Carlo Dose (GPUMCD) code disclosed in S. Hissoiny, B. Ozell, H. Bouchard, and P. Després, "GPUMCD: A new GPU-oriented Monte Carlo dose calculation platform," *Medical Physics*, 38(2):754-764, 2011, which is hereby incorporated by reference in its entirety. One skilled in the art will recognize that the GPUMCD code is used only for illustrative purposes and does not limit the scope of the methods and systems disclosed herein.

FIG. 1 depicts a schematic diagram of a system 100 for simulating radiation transport in radiotherapy, according to an embodiment. System 100 includes a processor 102, a storage medium 104, an input/output module 106, and a networking module 112. Processor 102 may be a central processing unit (CPU) that is known in the art, such as an INTEL processor or an AMD processor. In an embodiment, the CPU may be a general purpose processor. Storage medium 104 may be a volatile or non-volatile memory, such as a ROM, a RAM, a flash drive, a hard drive, a CD-ROM, a DVD-ROM, a register, and the like. Storage medium 104 may store computer codes including computer-executable instructions relevant to the simulation of the radiotherapy. Processor 102 may retrieve and execute the computer-executable instructions from storage medium 104, which may cause the processor 102 to perform any of the methods and/or steps according to the embodiments of this disclosure.

In addition, the storage medium 104 may also store data relevant to the simulation of the radiotherapy. The data may include material data representing known boundary materials, such as air, bone, and tissue, as discussed above. The known boundary materials may be stored in a table, which includes an identification or identifier for each boundary material. For example, the table may identify air, bone, and tissue as material 1, material 2, and material 3, respectively. Further the table may provide, for example, further indications for various types of tissue, as material 4, material 5, and material 6 for epithelial tissue, connective tissue, and nerve tissue, respectively.

The data in the storage medium 104 may also include, for example, patient-specific data such as images acquired prior to the radiotherapy. These images may be CT images, MRI images, X-ray images, ultrasound images, and the like. The processor 102 may generate a geometric model of the patient based on the image data. The geometric model may be a three-dimensional data set including a plurality of voxels representing a portion or an area of interest of the patient's body.

Based on the image data and the material data, processor 102 may further determine the material properties of each voxel, such as density, mass stopping power, and the like. The material properties may be generated during the simulation. Alternatively, the material properties of each voxel may be input into system 100 by a user prior to the simulation. The storage medium 104 may store material indices representing the material properties of all the voxels. The material indices of each voxel may identify the identifications of the materials within the voxel and the respective proportion of the materials. During simulation, the processor 102 may retrieve the material indices from the storage medium 104 and use the material indices to simulate the radiation transport between radioactive particles and the patient's body.

Input/output module 106 may include interfaces and circuits that communicate with peripheral devices, such as input device 108 and output device 110. Input device 108 may include, for example, a keyboard, a mouse, a touch pad, a light pen, and the like. The output device 110 may include, for example, a monitor or a projector. The system 100 may interact with a user through input device 108 and output device 110. For example, system 100 may receive user input through user input device 108. The user input may include parameters relevant to the simulation and modeling of the radiotherapy. Output device 110 may be a monitor or a projector configured to display simulations results to the user. Input device 108 and output device 110 may be integrated in a single device such as a touch screen that may both receive user input and provide user output. For instance the combined integrated device may be an iPad, a tablet, or a smartphone.

The networking module 112 may include interfaces or circuits that communicate with a computer network or other computer systems. For example, networking module 112 may include a Wi-Fi interface, an Ethernet interface, a Bluetooth interface, or other wireless or wired interfaces. The networking module 112 may allow system 100 to receive data and instructions relevant to the simulation of the radiotherapy. For instance, a hospital's computer network may be employed to provide data and instructions. For example, the system 100 may receive the material data and the patient-specific data through the networking module 112 and store both the material data and the patient specific data in the storage medium 104 for later retrieval.

According to an embodiment, based on the data and the boundary materials discussed above, system 100 may determine at least the following information for the model of the patient:
  a) The mass density of each voxel;
  b) Whether the voxel includes a mixture of two materials; and
  c) If the voxel includes a mixture, then the two boundary materials within the voxel and their proportions by volume. If the voxel does not include a mixture (i.e., a combination of two boundary materials), then the material index of the voxel;

Therefore, all voxels may include a mixture of at least two boundary materials. In some voxels, one material may have a proportion of zero and the other material may have a proportion of one; thereby indicating no mixture. Thus, system 100, like conventional Monte Carlo dose modeling system, is compatible with a model having voxels each containing only one material. Unlike conventional systems, however, system 100 may also model a combination of two or more materials within a single voxel and a continuous variation of the two or more materials within the model of the patient.

According to another embodiment, system 100 may assign a material index to each voxel. If the material index of a specific voxel has no fractional part, then the voxel contains a pure boundary material. If, on the other hand, the material index of a voxel has a fractional part (e.g., n.5), then the voxel contains a mixture of boundary materials n and n+1. Here, n is an integer representing the identifier of the nth boundary material in the list of boundary materials discussed above.

According to another embodiment, system 100 may generate a CMI identifier (e.g., continuous material index) for every voxel based on input data, such as the boundary materials and the patient-specific data discussed above. The CMI identifiers for all the voxels may be generated at run time. For example, a material index of a voxel may have a form of x.y including an integer part x and a fractional part y. The integer part identifies a first material in the combination of materials that are present within a given voxel. The fractional part y represents a percentage of the voxel that is made up by a second material in the combination. As another example, when the material boundaries include air, soft tissue, and bone, as described above, a CMI index of 1.26 for a voxel including tissue and bone indicates that the voxel contains a combination of 74% tissue by volume and 26% bone by volume. The percentage of the voxel indicated by the fractional part of the material index may in another embodiment also represent a percentage in mass or weight.

System 100 may compute the relative percentages based on input data indicating that a given voxel contains a mixture of two materials and has a given density. The computation relies on the fact that intrinsic densities of the pure materials are known. For example, water, soft tissue, and cortical bone have, respectively, intrinsic densities of 1.00 g/cc, 1.06 g/cc, and 1.85 g/cc, which are known and may be input into or stored in system 100. System 100 may then compute the percentage of the second material within a voxel according to the following formula:

$$f_2 = \frac{\rho - \rho_1}{\rho_2 - \rho_1}, \quad (1)$$

where $f_i$ is the relative percentage of the i'th material, $\rho$ is the density of the voxel, and $\rho i$ is the intrinsic density of the i'th boundary material.

According to another embodiment, during simulation of radiotherapy, system 100 may establish material properties at a given location within the patient's body using two pieces of information for every voxel: the mass density and the material identifier. The material identifier is used to fetch the material-specific properties (e.g., mass attenuation coefficient, mass stopping power, mass scattering power, and the like), and the mass density is used to obtain the values of the material-specific quantities.

According to an embodiment, system 100 may determine the material properties at a given location within the patient's body and use the material properties to model a discrete interaction between a particle and the patient's body. An interaction type between the particle and the voxel may be sampled based on the properties of the material within the voxel. In this embodiment, the interaction between the particle and the voxel may only take place in one material, which is randomly sampled from the two materials present in the voxel.

System 100 may use the GPUMCD technique discussed above based on Woodcock tracking, in which the linear attenuation coefficient for all voxels across the phantom is assumed to be a constant, for particles such as photons or electrons. As a result, the interaction probability per unit path length is constant, but there is a higher probability of a fictitious interaction in materials of lower density or lower mass attenuation coefficient. The probability that the interaction point lies in the first material (i.e., material 1) within a voxel is thus equal to the fraction of the path length that goes through the first material, which is taken to be equal to the fraction of the voxel occupied by the first material. The sampling is thus based on the relative percentage of the two materials in the voxel.

In this embodiment, system 100 may generate a uniform random number and determine if the random number is lower than the relative percentage of the second material, represented by the fractional part y of the material index (i.e., the CMI index). If the random number is lower than the percentage of the second material, then system 100 uses the properties of the second material for sampling the interaction type and computes the effects of the interaction. Otherwise, system 100 uses the properties of the first material.

According to an alternative embodiment, system 100 may define a line to model a track of a moving particle that is traveling across a voxel. System 100 may then determine the material properties along the line and determine how much energy is deposited in the voxel, based on the material properties of the voxel and the distance traveled by the particle in the voxel. System 100 may assume that a fraction $f_1$ of a track is within a first material (material 1) and another fraction $f_2=1.0-f_1$ is within a second material (material 2). Accordingly, system 100 may determine the energy deposited by the particle within the voxel according to the following formula:

$$E_{dep}=L(f_1 S_1+f_2 S_2), \quad (2)$$

where $E_{dep}$ is the energy deposited in the voxel, L is the distance traveled by the particle in the voxel, $S_i$ is the restricted total linear stopping power of the i'th material.

Alternatively, the energy deposited in the voxel may also be determined according to the following formula:

$$E_{dep}=L(f_1\rho_1+f_2\rho_2)s_{\textit{eff}}, \quad (3)$$

where $s_{\textit{eff}}$ may be determined according to the following formula:

$$s_{\textit{eff}} = \frac{(f_1\rho_1 s_1 + f_2\rho_2 s_2)}{(f_1\rho_1 + f_1\rho_1)}, \quad (4)$$

where $s_1$ and $S_2$ represent the mass stopping power of the first material and the second material, respectively.

According to another embodiment, system 100 may also determine a dose to a reference medium (DTRM), such as dose to water (DTW), according to the following formula:

$$E_{DTRM} = L\left(f_1\rho_1 s_1 \frac{s_{ref}}{s_1} + f_2\rho_2 s_2 \frac{s_{ref}}{s_2}\right), \text{ or} \quad (5)$$

$$E_{DTRM} = L(f_1\rho_1 s_1 + f_2\rho_2 s_2)s_{ref}, \quad (6)$$

where $s_{ref}$ is the restricted total mass stopping power of the reference material.

According to another embodiment, system 100 may also determine other quantities that accumulate along the track of the particle. For example, system 100 may determine effective values for the multiple scattering parameters $b_c$ and $\chi_{cc}^2$, which are energy-independent material properties that govern multiple scattering, using formulas similar to equation (2) above. To this end, $S_i$ in equation (2) may be replaced by the property of interest (e.g., $b_c$ or $\chi_{cc}^2$) in calculating the effective values.

Figure 2:
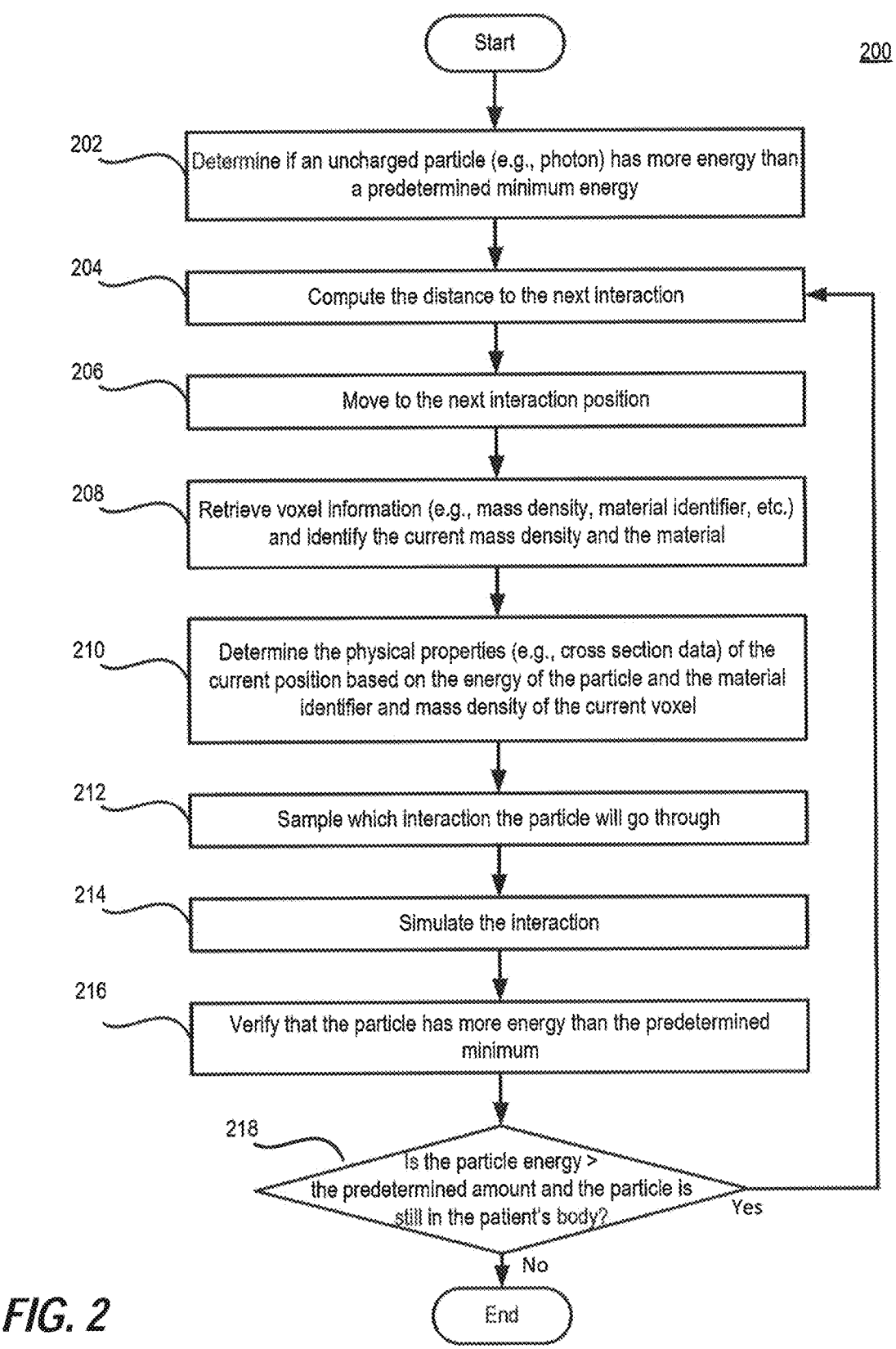
FIG. 2 is a flowchart for a process of simulating transport of uncharged particles for purposes of radiotherapy dose calculation, according to an embodiment of the disclosure.

FIG. 2 illustrates an exemplary method for simulating radiation transport between particles and the patient's body during radiotherapy, consistent with a disclosed embodiment. In particular, FIG. 2 depicts a process 200 for simulating radiation transport based on continuous material indices for uncharged particles, such as photons. Process 200 may be implemented by system 100.

According to FIG. 2, at step 202, system 100 determines whether an uncharged particle, such as a photon, has more energy than a predetermined minimum energy that has been defined by the user. If yes, process 200 continues to step 204. If no, process 200 terminates. At step 204, system 100 computes a distance to the next point of interaction between the particle and the patient's body. At step 206, system 100 simulates a movement of the particle to the next point of interaction determined at step 204. As a result, the next point of interaction becomes a current point of interaction. At step 208, system 100 retrieves voxel information, such as the mass density, the material index, and the like, of the voxel at the current point of interaction and identifies the boundary materials and the corresponding mass density at the current point of interaction.

At step 210, system 100 determines the physical properties, such as cross section data, of the current point of interaction based on the energy of the particle and the material index and the mass density of the current voxel using the processes defined above in equations (5) and (6). At step 212, system 100 determines which interaction the particle will go through according to known techniques that determine the cross section of every interaction type. At step 214, system 100 simulates the interaction between the particle and the current voxel according to the Monte Carlo technique. At step 216, system 100 verifies that the particle has more energy than the predetermined minimum energy. At step 218, if the particle has more energy than the predetermined minimum energy, then process 200 returns to step 204 for the next iteration. Process 200 continues the iterations until the energy of the particle becomes less than the predetermined amount or the particle exits the patient's body.

Figure 3:
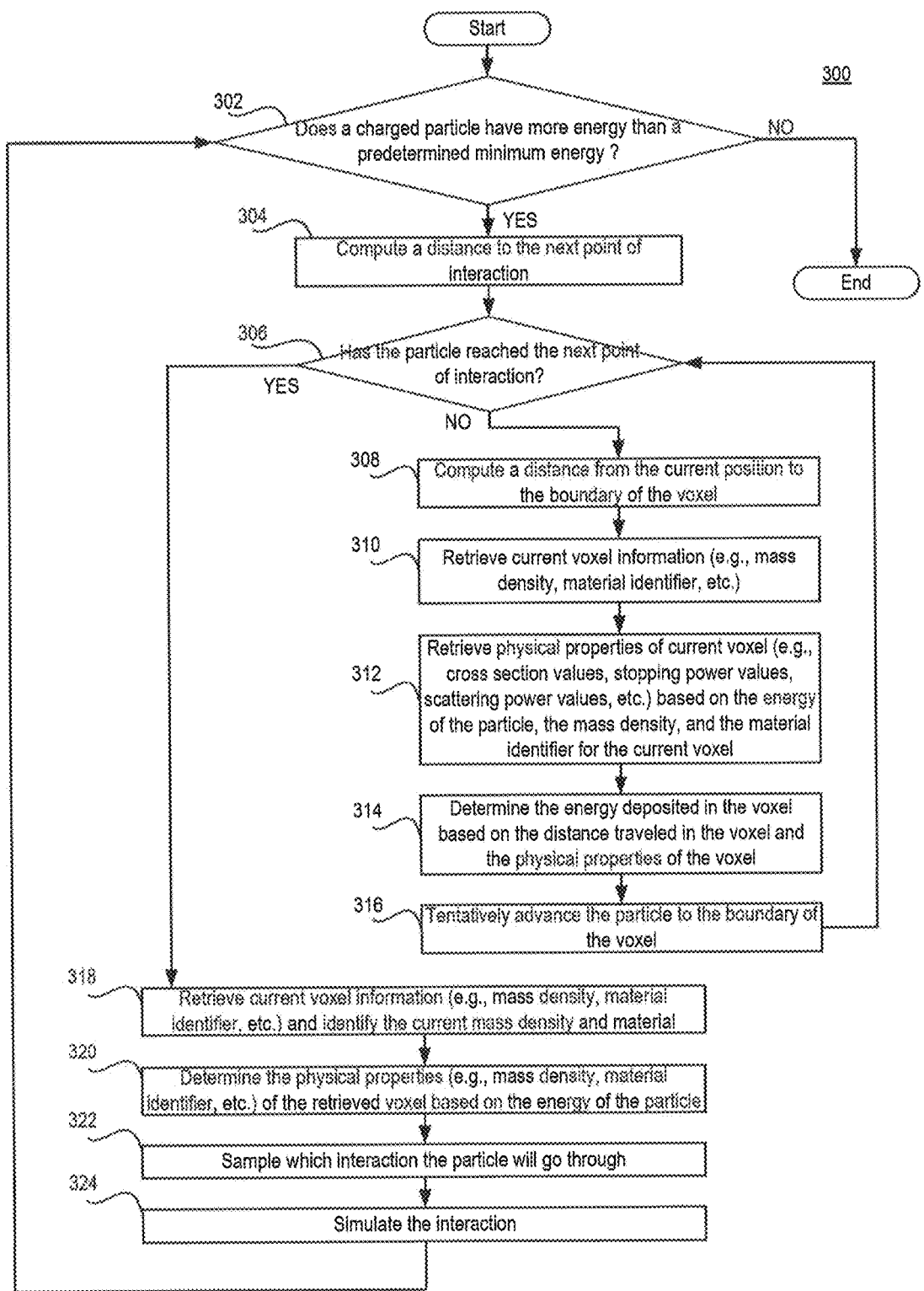
FIG. 3 is a flowchart for a process of simulating transport of charged particles for purposes of radiotherapy dose calculation, according to another embodiment of the disclosure.

FIG. 3 depicts a process 300 for simulating radiation transport based on continuous material indices for charged particles, such as electrons, consistent with a disclosed embodiment. Process 300 may also be implemented on system 100 described above. According to FIG. 3, at step 302, system 300 determines whether a particle has more energy than a predetermined minimum energy and if the particle is still in the patient's body. If yes, process 300 continues to step 304. If no, process 300 terminates. At step 304, system 100 computes a distance to the next point of interaction between the particle and the patient's body. At step 306, system 100 determines whether the particle has reached the position of the next point of interaction. If yes, process 300 continues to step 318. If no, process 300 continues to step 308.

At step 308, system 100 computes a distance from the current position of interaction to the boundary of the voxel. At step 310, system 100 retrieves the information of the current voxel, such as the mass density, the material index, and the like. At step 312, system 100 retrieves physical properties of the current voxel, such as the cross section values, the stopping power values, the scattering power values, based on the energy of the particle, the mass density, and the material index for the current voxel. At step 314, system 100 determines the energy deposited in the voxel based on the distance traveled in the voxel and the physical properties of the voxel. At step 316, system 100 tentatively advances the particles to the boundary of the voxel. Process 300 then returns to step 306.

At step 318, system 100 retrieves information of the current voxel, such as the mass density, the material index, and the like. At step 320, system 100 determines the physical properties of the current voxel, such as the mass density, the material identifier, and the like, based on the energy of the particle. At step 322, system 100 determines which interaction the particle will go through and samples the interaction. At step 324, system 100 simulates the interaction between the particle and the voxel according to the Monte Carlo technique. Thereafter, process 300 then returns to step 302 and continues to the next iteration.

Although FIG. 2 and FIG. 3 describe embodiments of simulating radiation transport based on continuous material indices for uncharged particles (e.g., photons) and charged particles (e.g., electrons), respectively, as known by those skilled in the art, the described process is not limited to these types of particles.

According to an embodiment, the continuous material indexing (CMI) method disclosed herein may be implemented in the GPUMCD code described above. Results generated by the GPUMCD code with and without CMI are compared to evaluate the performance of the CMI. In this embodiment, all tests are performed with a field size of approximately 1.5 cm by 1.5 cm on the surface of a phantom. The tests are run until an uncertainty of approximately 0.25% is reached. Chemical compositions of the boundary materials are provided in "Tissue Substitutes in Radiation Dosimetry and Measurement," Technical Report No. 44, International Commission on Radiation Units and Measurements (ICRU), Bethesda, Md., 1989, which is hereby incorporated by reference. The chemical compositions and the mass densities of some exemplary boundary materials are listed in Table 1 of FIG. 4.

According to a further embodiment, a first test may test three different models, including: geometry 1: thin layers of alternating discrete materials; geometry 2: coarse layers of pre-mixed homogeneous material; and geometry 3: coarse layers of a mixture defined by continuous material indexing. All three models may include soft tissue and bone, and are equivalent in terms of the quantity of bone material present therein. The three models may be labeled as a reference model, a mixture model, and a CMI model, respectively. The goal of using these three different models is to show that the CMI model produces equivalent or better results than the reference and mixture models, which correspond to conventional techniques. The CMI model also shows that the CMI technique is valid for all geometries including all material types. Additionally, for the mixture and the CMI geometries, the DTRM with the reference material set to soft tissue is computed. A 24 MeV electron beam is simulated, because electron beams are more sensitive to material differences.

The reference model may use 0.1 mm deep voxels. For example, for a slab with a thickness of 10 voxels, the voxel layers alternate between cortical bone at 1.92 g/cc and tissue at 1.06 g/cc. Thus, within a slab with a thickness of 1.0 cm, there is 50% soft tissue by volume and 50% cortical bone by volume.

The mixture model may use 0.2 mm deep voxels. For example, for a slab with a thickness of 5 voxels or 1.0 cm, the pre-mixed material that represents a mixture of 50% bone and 50% soft tissue is used at a density of 1.49 g/cc.

The CMI model may use 0.2 mm deep voxels. For example, for a slab with a thickness of 5 voxels or 1.0 cm, the voxels are identified as having a CMI index with boundary materials of tissue and bone and a voxel mass density of 1.49 g/cc.

Figure 5:
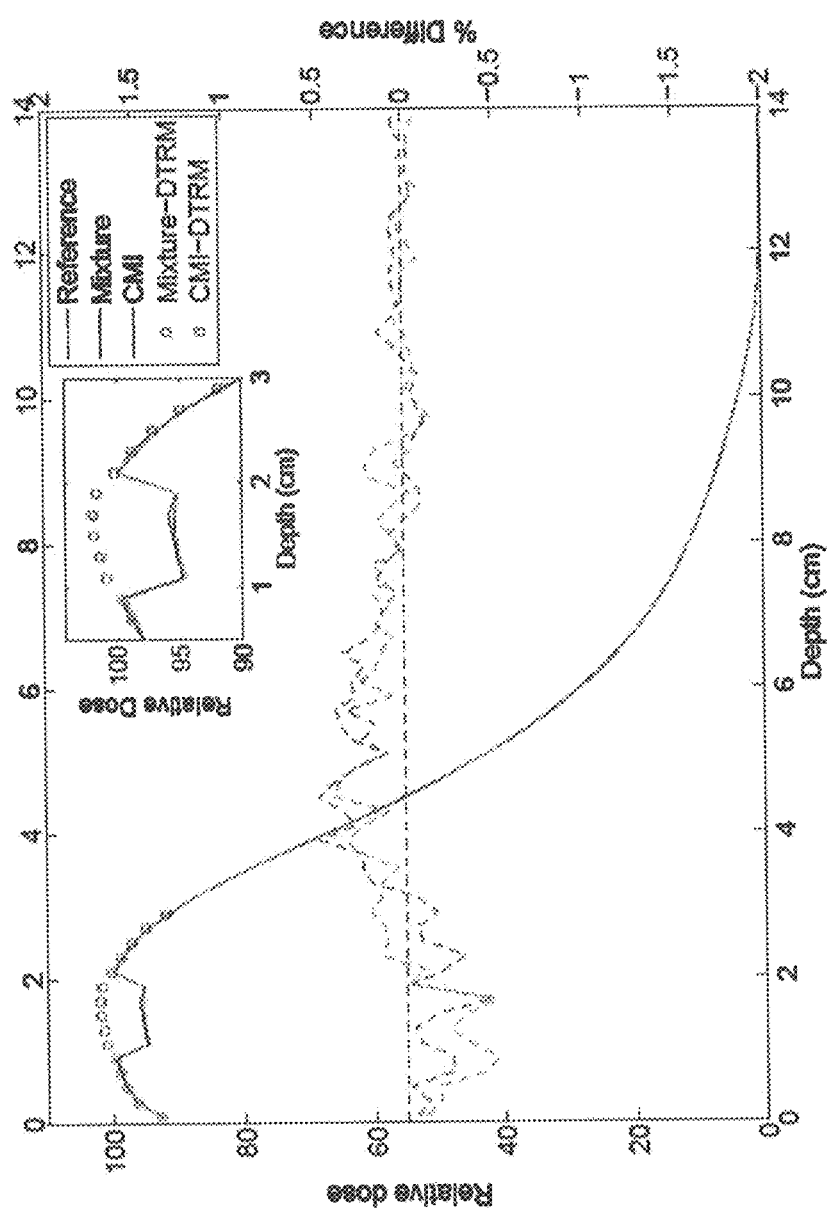
FIG. 5 shows results of a test conducted according to an embodiment of the disclosure.

The results for the first test described above with the 24 MeV electron beam are presented in FIG. 5. In FIG. 5, solid lines represent dose results, and dashed lines represent difference results. The dose results are absolutely normalized and then rescaled so that the maximum value of the reference distribution is equal to 100. All the difference results are computed as $val_{test}$–$val_{ref}$ for the data that has been rescaled. The insert in FIG. 5 is a close-up view of the heterogeneity region. The dose-to-medium values are reported in both cases. The dose-to-tissue results are also inserted in the graph using the 'o' markers. The DTRM results are limited to the region around the bone slab in order to reduce clutter.

System 100 may further process the reference PDD data to interpolate the results on the same resolution as the tested models. In particular, for all voxels, the dose to the voxel is multiplied by the mass of the voxel to get the energy deposited. For successive pairs of voxels (e.g., voxel 1 with voxel 2, or voxel 3 with voxel 4), the energy deposited in the first voxel is added to the energy deposited in the second voxel and stored in an energy deposition plot with the resolution of the test geometry. Finally, each value in the energy deposition plot is divided by the combined mass of the two original voxels to get the absorbed dose in the combined voxel.

Within the heterogeneity region in FIG. 5, i.e., from a depth of 1.0 to 2.0 cm, the agreement between all curves is within 0.5%. Immediately after the heterogeneity region, all curves are within 1% agreement, and remain so for the remaining region. One skilled in the art will recognize that the reference PDD does not necessarily represent a ground truth, against which the other results are evaluated. It represents a specific situation of alternating bone and tissue layers, starting with bone. The reference data is different if the alternating layers start with soft tissue.

According to another embodiment, a second test may evaluate the behavior of the CMI method when a physical interface cuts across the interior of a voxel. In this embodiment, an interface between two different boundary materials does not coincide with the voxel grid. The reference model represents the underlying physical phantom including 200 voxels, where each voxel is 1.0 mm deep, with an interface between soft tissue and bone at a depth of 5.1 cm. The model representing the underlying physical phantom is downsampled by reducing the resolution to a dose grid of less than sufficient resolution to capture substantial details of the phantom, such as 100 2.0 mm voxels. The interface cannot be described sharply at this resolution, because it falls in the middle of the $26^{th}$ voxel. Accordingly, the $26^{th}$ voxel is half soft tissue and half bone and is, thus, assigned a density of 1.49 g/cc. When utilizing the mixture model, the mixture model is assigned the pre-defined medium that is half soft tissue and half bone. When utilizing the CMI model, the CMI model is assigned a CMI medium index indicating equal parts soft tissue and bone. The simulation uses a 24 MeV electron beam.

Figure 6:
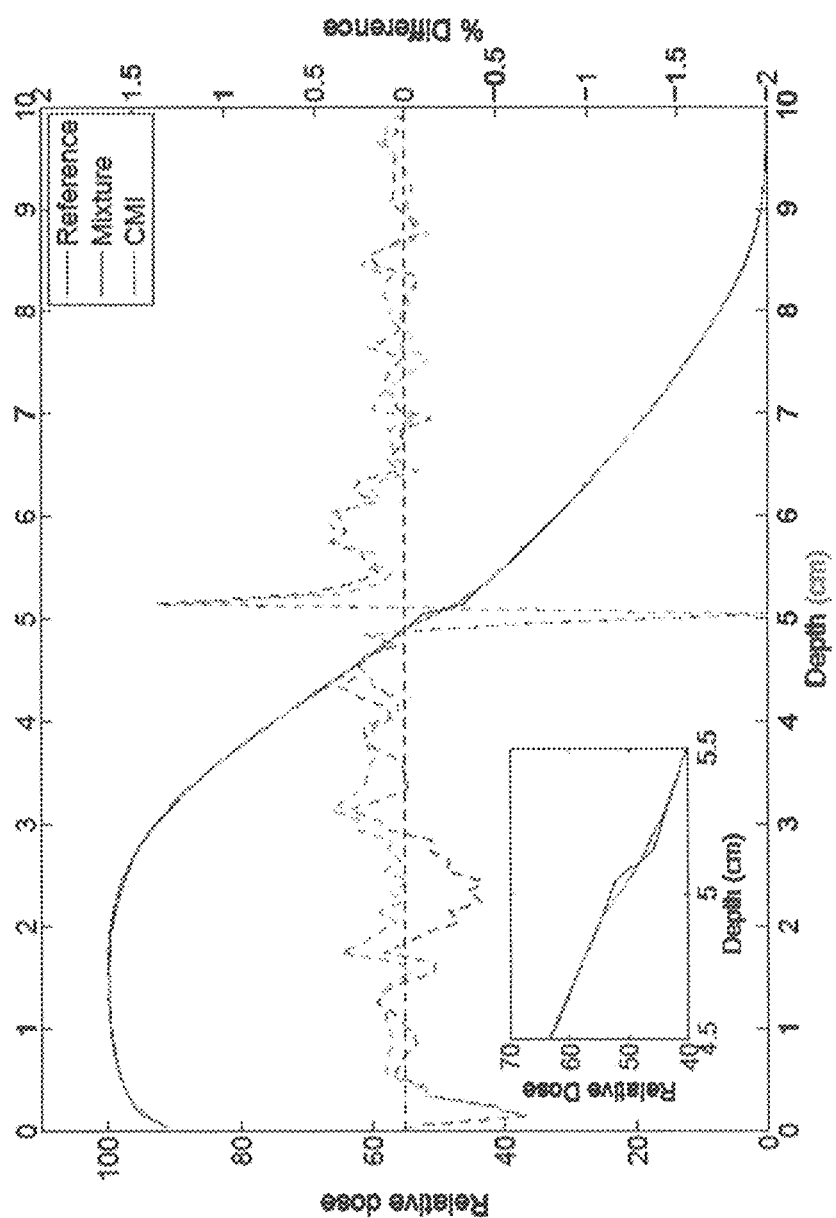
FIG. 6 shows results of a test conducted according to another embodiment of the disclosure.

The results for the second test discussed above, with a sharp interface, are presented in FIG. 6. Similarly, in FIG. 6, solid lines represent dose results, and dashed lines represent difference results. The dose results are absolutely normalized and then rescaled so that the maximum value of the reference distribution is equal to 100. All the difference results are computed as $val_{test}$–$val_{ref}$ on the data that has been rescaled. The insert in FIG. 6 is a close-up view of the interface that is located at a depth of 5.1 cm.

As shown in FIG. 6, large differences between the reference distribution and the other distributions are visible within the interface voxel itself. These differences are expected because the physical reality in both situations is not the same. In the reference case, the materials at 1 mm before the interface include soft tissue, and the materials at 1 mm after the interface include bone. In the other cases, however, the materials within 2 mm around the interface isotropically include a 50%-50% mixture of soft tissue and bone. Both the mixture and the continuous geometries behave in the same way before, within, and after the interface, which is the expected result. The differences between the reference and the test distributions at shallow depths are likely caused by voxel size effects. The two test distributions at the same voxel resolution agree with each other.

Advantageously, by using Monte Carlo simulation, a patient's body that is subject to radiotherapy is modeled as a three-dimensional data set including a plurality of voxels. The process determines the radiation transport by determining the distance traveled by a particular particle and the type of interaction between the particle and the voxels.

Each voxel may represent a value on a regular grid in a three-dimensional space. Material information representing physical and material properties for every voxel is defined, where the materials are not specific to a given patient or a treatment plan. Each voxel, for example, may contain one or more boundary materials. The material of a particular single voxel is determined as a combination of at least two or more boundary materials. Advantageously, unlike conventional systems, the percentages of the boundary materials within individual voxels may vary continuously from voxel to voxel for the patient model.

Further, a decimal number may be used advantageously to model the fact that a voxel is filled with a combination of two or more materials or substances, rather than only one material in order to conform to the physical reality in which materials, such as a combination of air and soft tissue or a combination of bone and soft tissue, are not mixed homogeneously within a voxel, but rather occupy geometrically discrete portions of the voxel. The material properties at a given location within the patient's body are established using two pieces of information for every voxel: the mass density and the material identifier. The material identifier is used to fetch the material-specific properties (e.g., mass attenuation coefficient, mass stopping power, mass scattering power, and the like), and the mass density is used to obtain the values of the material-specific quantities. These material indices (e.g., such as mass density, the material identified, and the like) identify the materials within the voxel and their respective proportions, which are used to determine the current physical properties of the current voxel.

Based on the physical properties of the voxel, the radiation transport between the radioactive particles and the patient's body may be determined by determining the distance traveled by a particular particle (e.g., charged, uncharged, and other types of particles) and the type of interaction between the particle and the voxels.

Other embodiments will be apparent to those skilled in the art from consideration of the specification and practice of the disclosed embodiments. It is intended that the specification and examples be considered as exemplary only, with a true scope and spirit of the disclosed embodiments being indicated by the following claims.

What is claimed is:

1. A computer-implemented method for simulating energy transport between particles and a patient in radiotherapy, utilizing at least one processor, comprising:
   using a three-dimensional representation of a region of interest in the patient that includes voxels, identifying a plurality of boundary materials for an individual voxel in the patient and a plurality of identifiers associated with the plurality of boundary materials;
   selecting from the plurality of boundary materials for the individual voxel, a combination of a first boundary material and a second boundary material for the individual voxel based on a material property of the individual voxel, wherein the first boundary material is different from the second boundary material;
   determining a continuous material index for the individual voxel based on the combination of the first boundary material and the second boundary material, wherein the continuous material index represents respective volumetric proportions of the first boundary material and the second boundary material for the individual voxel;
   simulating energy transport between a particle and the individual voxel by calculating an amount of energy deposited by the particle within the individual voxel based on the continuous material index, including simulating an interaction between the particle and the individual voxel, the interaction taking place in one of the first or second boundary material that is randomly chosen from the first and second boundary materials present in the individual voxel; and
   generating a display using the simulated energy transport between the patient and the particles.

2. The computer-implemented method of claim 1, wherein selecting the combination of the first boundary material and the second boundary material further comprises determining percentage compositions of the first boundary material and the second boundary material in the individual voxel.

3. The computer-implemented method of claim 2, wherein calculating the amount of energy deposited by the particle within the individual voxel further comprises:
   randomly choosing, from the first and second boundary materials, one boundary material in which the interaction takes place, wherein probabilities of choosing the first and second boundary materials are proportional to the percentage compositions of the first and second boundary materials, respectively.

4. The computer-implemented method of claim 2, wherein the material index includes a first part corresponding to one of the plurality of identifiers that identifies the first boundary material and a second part corresponding to the percentage composition of the second boundary material.

5. The computer-implemented method of claim 4, wherein calculating the amount of energy deposited by the particle within the individual voxel further comprises:
   generating a random number;
   determining whether the random number is lower than the second part of the material index;
   when it is determined that the random number is lower than the second part of the material index, choosing the second boundary material for simulating the interaction; and
   when it is determined that the random number is equal to or larger than the second part of the material index, choosing the first boundary material for simulating the interaction.

6. The computer-implemented method of claim 5, wherein calculating the amount of energy deposited within the individual voxel further comprises simulating the interaction between the particle and the individual voxel according to a Monte Carlo technique.

7. The computer-implemented method of claim 1, wherein the material property of the individual voxel includes a material density of the individual voxel.

8. The computer-implemented method of claim 1, wherein calculating the amount of energy deposited by the particle further comprises calculating a distance traveled by the particle within the individual voxel.

9. The computer-implemented method of claim 1, wherein the particle is at least one of a charged particle or an uncharged particle.

10. The computer-implemented method of claim 9, wherein the particle is an electron.

11. The computer-implemented method of claim 9, wherein the particle is a photon.

12. The computer-implemented method of claim 1, further comprising determining whether an amount of energy of the particle is greater than a minimum value.

13. The computer-implemented method of claim 1, wherein the individual voxel includes a tumor or an organ of interest in the patient.

14. A system for simulating energy transport between particles and a patient undergoing radiotherapy, comprising:
   a memory for storing computer-executable instructions; and
   a processor for executing the computer-executable instructions to perform instruction operations comprising:
      generating a three-dimensional representation of a region of interest of a patient that includes voxels;
      using the three-dimensional representation, identifying a plurality of boundary materials within an individual voxel;
      selecting from the plurality of boundary materials within the individual voxel, a combination of a first boundary material and a second boundary material for the individual voxel based on a material property for the individual voxel, wherein the first boundary material is different from the second boundary material;
      determining a material index of the individual voxel based on a combination of the first and second boundary materials and identifiers assigned to the boundary materials, the material index for the individual voxel having a first part including an identifier of only the first boundary material within the individual voxel and a second part including a percentage of the individual voxel associated with the second boundary material;
      simulating energy transport between a particle and the individual voxel by calculating an amount of energy deposited by the particle within the patient based on the material index of the individual voxel and a list of boundary materials; and
      generating a display using the simulated energy transport between the patient and the particles.

15. The system of claim 14, further comprising:
   determining a distance traveled by the particle within the individual voxel, wherein calculating the amount of energy deposited by the particle within the patient is further based on the distance.

16. The system of claim 15, wherein the material index further comprises information of material properties of the boundary materials.

17. The system of claim 16, wherein the material properties of the boundary materials comprise at least one of stopping power, scattering power, or attenuation coefficient.

18. The system of claim 14, further comprising:
determining the percentage of the individual voxel associated with the second boundary material based on a density of the individual voxel, a density of the first boundary material, and a density of the second boundary material.

19. A non-transitory computer-readable medium including computer-executable instructions, which, when executed by a processor, cause the processor to perform a method for simulating energy transport between particles and an object in radiotherapy, the method comprising:
using a three-dimensional representation of a region of interest in the patient that includes voxels, identifying a plurality of boundary materials for an individual voxel and a plurality of identifiers associated with the plurality of boundary materials;
selecting, from the plurality of boundary materials for the individual voxel, a combination of a first boundary material and a second boundary material for the individual voxel based on a material property of the individual voxel;
determining a continuous material index for the individual voxel based on the combination of the first boundary material and the second boundary material, wherein the continuous material index represents respective volumetric proportions of the first boundary material and the second boundary material for the individual voxel;
simulating energy transport between a particle and the individual voxel by calculating an amount of energy deposited by the particle within the individual voxel based on the continuous material index, including simulating an interaction between the particle and the individual voxel, the interaction taking place in one of the first or second boundary material that is randomly chosen from the first and second boundary materials present in the individual voxel; and
generating a display using the simulated energy transport between the patient and the particles.

20. The non-transitory computer-readable medium of claim 19, wherein selecting the combination of the first boundary material and the second boundary material further comprises comparing a density of the individual voxel with densities of the plurality of boundary materials.

21. The non-transitory computer-readable medium of claim 20, wherein determining the material index further comprises determining a first percentage of the individual voxel associated with the first boundary material and a second percentage of the individual voxel associated with the second boundary material.

22. The non-transitory computer-readable medium of claim 21, wherein the material index comprises a first part including the identification of the first boundary material and a second part including the second percentage of the individual voxel.

23. The non-transitory computer-readable medium of claim 19, wherein the object is a tumor or an organ of interest in a patient.

24. A computer-implemented method for simulating energy transport between particles and a patient in radiotherapy, utilizing at least one processor, comprising:
using a three-dimensional representation of a region of interest in the patient that includes voxels, identifying a plurality of boundary materials for an individual voxel in the patient and a plurality of identifiers associated with the plurality of boundary materials;
selecting from the plurality of boundary materials for the individual voxel, a combination of a first boundary material and a second boundary material for the individual voxel based on a material property of the individual voxel, wherein the first boundary material is different from the second boundary material;
determining a continuous material index for the individual voxel based on the combination of the first boundary material and the second boundary material, wherein the continuous material index represents respective volumetric proportions of the first boundary material and the second boundary material for the individual voxel;
simulating energy transport between a particle and the individual voxel by calculating an amount of energy deposited by the particle within the individual voxel based on the continuous material index, including simulating an interaction between the particle and the individual voxel, the interaction taking place in one of the first or second boundary material that is randomly chosen from the first and second boundary materials present in the individual voxel; and
displaying the energy transport simulations to a user.

25. A computer-implemented method for simulating energy transport between particles and a patient in radiotherapy, utilizing at least one processor, comprising:
using a three-dimensional representation of a region of interest in the patient that includes voxels, identifying a plurality of boundary materials for an individual voxel in the patient and a plurality of identifiers associated with the plurality of boundary materials;
selecting from the plurality of boundary materials for the individual voxel, a combination of a first boundary material and a second boundary material for the individual voxel based on a material property of the individual voxel, wherein the first boundary material is different from the second boundary material;
determining a continuous material index for the individual voxel based on the combination of the first boundary material and the second boundary material, wherein the continuous material index represents respective volumetric proportions of the first boundary material and the second boundary material for the individual voxel;
simulating energy transport between a particle and the individual voxel by calculating an amount of energy deposited by the particle within the individual voxel based on the continuous material index, including simulating an interaction between the particle and the individual voxel, the interaction taking place in one of the first or second boundary material that is randomly chosen from the first and second boundary materials present in the individual voxel; and
using the simulated energy transport to plan or manage radiotherapy delivered to the subject.

* * * * *

UNITED STATES PATENT AND TRADEMARK OFFICE
CERTIFICATE OF CORRECTION

PATENT NO. : 10,292,670 B2
APPLICATION NO. : 14/271862
DATED : May 21, 2019
INVENTOR(S) : Sami Hissoiny Page 1 of 1

It is certified that error appears in the above-identified patent and that said Letters Patent is hereby corrected as shown below:

On page 2, in Column 2, under "Other Publications", Line 32, delete "PCT/182014/066493," and insert --PCT/IB2014/066493,-- therefor Signed and Sealed this
Twenty-first Day of April, 2020

Andrei Iancu
*Director of the United States Patent and Trademark Office*